United States Patent [19]

Shetty et al.

[11] Patent Number: 5,405,767
[45] Date of Patent: Apr. 11, 1995

[54] PURIFIED ENZYME CONCENTRATE AND METHOD OF PREPARATION

[75] Inventors: Jayarama K. Shetty, Elkhart; Chimanbhai P. Patel, Mishawaka, both of Ind.

[73] Assignee: Solvay Enzymes, Inc., Houston, Tex.

[21] Appl. No.: 865,252

[22] Filed: Apr. 8, 1992

[51] Int. Cl.$^6$ .......................... C12N 9/14; C12N 9/24; C12N 9/54
[52] U.S. Cl. ..................................... 435/195; 435/200; 435/212; 435/219; 435/220; 435/221; 435/222; 435/816
[58] Field of Search ................ 435/188, 195, 212, 219, 435/220, 221, 222, 816

[56] References Cited

U.S. PATENT DOCUMENTS

| | | | |
|---|---|---|---|
| 3,050,445 | 8/1962 | Damaskus et al. | 435/188 |
| 4,497,897 | 2/1985 | Eilertsen et al. | 435/188 |
| 4,507,219 | 3/1985 | Hughes | 252/118 |
| 4,747,977 | 5/1988 | Whitehead et al. | 252/111 |

Primary Examiner—Douglas W. Robinson
Assistant Examiner—L. Blaine Lankford
Attorney, Agent, or Firm—Willian Brinks Hofer Gilson & Lione

[57] ABSTRACT

A novel compound for producing a purified enzyme precipitate and a method of preparing the purified enzyme precipitate, wherein the compound is an organic compound selected from the group consisting of carboxylic acids having at least 2 carboxyl groups, salts or esters of these carboxylic acids, amino acids, salts or esters of these amino acids.

20 Claims, No Drawings

PURIFIED ENZYME CONCENTRATE AND METHOD OF PREPARATION

BACKGROUND INFORMATION

The present invention relates to the recovery and purification of enzymes from fermentation preparations, and the purified enzyme product that results therefrom.

The use of enzymes in detergents is well known. Generally, enzymes used in detergents have primarily been the alkaline stable proteases, lipases and alpha-amylases. Of the alkaline proteases, serine proteases derived from Bacillus species, namely *Bacillus subtilis, Bacillus licheniformis*, and alkalophilic Bacillus bacteria have been widely used in detergent formulations. (Starace, C. and Barford, H. C., *Encyclopedia Chem. Technol.* 9, pp. 138-148 (1980); Koki Horikoshi and Terahiko Akika, *A New Microbial World*, Springer-Verlag, New York, p. 93 (1982)).

Enzymes constitute only a small portion of most liquid detergent formulations. Thus, it is necessary to produce fairly concentrated enzyme preparations. Enzyme concentrates are traditionally prepared by removing the water from aqueous solutions of the enzymes using conventional methods such as ultrafiltration and evaporation.

Inorganic salts such as ammonium sulphate and sodium sulphate have been used extensively to precipitate enzymes from aqueous solution at both the laboratory and commercial levels. (Dixon, M. and Webb, E. D., *Enzymes*, Academic Press, N.Y., pp. 39-41 (1964), Curline, *Methods of Plasma Protein Fractionation*, Academic Press, New York (1980)). The widespread use of these salts on a large scale, however, can pose environmental problems and complicate waste water treatment. In fact, many countries in Europe have already restricted large scale industrial use of these salts. Organic solvents such as ethanol and acetone are also used as precipitants (Dixon and Webb, *Enzymes*, supra, pp. 37-39; Bauer et al,. *J. Chem.*, 5(3), pp. 117-20 (1967)), however, their use has been limited because of cost and concern for safety.

The color and odor of enzymes can adversely effect the quality of the detergent formulations in which they are incorporated. This necessitates the removal of pigments from the enzyme concentrate, which pigments are believed to be a part of an enzyme-pigment complex. Dixon, M. and Webb, E. C., *Enzymes*, supra, reported solvent precipitation methods to remove pigment from protease solution. This method, however, resulted in poor product yield. Absorption of pigments with activated carbon from aqueous enzyme concentrate is generally practiced in industrial applications, however, material loss, high cost and waste disposal present major drawbacks.

It is desirable that enzyme preparations for detergent applications be free from components which can cause undesirable color, haze, instability and allergic activity in the final product. These components may be derived from the microorganism themselves or from residual fermentation raw materials. In preparations of gram positive Bacilli, cell wall anionic polymers, peptidoglycans, galactosyl polymers, and other polysaccharide contaminants become solubilized during cell growth due to cell wall turnover. The presence of these bacterial cell wall polymers in enzyme preparations can cause several undesirable effects including an increase in the allergenicity, a decrease in enzyme stability by binding cations, e g., $Ca^{++}$, and may cause haze formation in detergent formulations.

In U.S. Pat. No. 4,659,667 a method for crystallization of an enzyme is disclosed wherein the pH of the super saturated enzyme solution is adjusted to its isoelectric pH.

In U.S. Pat. No. 4,699,882 a method for crystallization of glucose isomerase using ammonium and magnesium sulphate is disclosed.

In Patent Cooperation Treaty ("PCT") Application No. WO89/05863 published Jun. 29, 1986, a method for separation of the galactosyl polymer associated with allergenic activity from protease preparations is described using ion-exchange chromatography.

In U.S. Pat. No. 5,041,377, a method for obtaining crystalline subtilisin is described where in subtilisin derived from *Bacillus subtilis* and *Bacillus amyloliquifaciens* is crystallized by the addition of a halide salt (sodium chloride and potassium chloride) to an alkaline protease solution at low temperature.

In PCT Application WO 91/09943 a method for the crystallization of enzymes is described where an aqueous enzyme containing liquid with a relatively high enzyme purity and with a concentration of pure enzyme protein of at least 5 g/l is used as a starting material, and a crystallization agent which is an easily soluble salt of the non-halide type, such as Na, K, Ca, or Mg formate, acetate or nitrate, is added to the starting material. In the examples using proteases, the starting material is prepared by sodium sulphate precipitation.

None of the patents, patent applications or publications described above provide the important advantages of a simple and efficient method of preparing a purified enzyme preparation free from contaminants wherein a high yield of purified enzyme is obtained, and the use of inorganic salts or other nonbiodegradable compounds is avoided.

SUMMARY OF THE INVENTION

It is an object of this invention to provide for a novel method of purifying enzymes so as to remove pigments and other contaminants associated with haze, color contamination and odor in commercial enzyme preparations.

It is a further object of this invention to provide for a simple and novel method for the purification of enzymes which removes polysaccharides and oligosaccharides and other galactosyl polymers which are responsible for problems associated with allergenic activity.

It is a further object of this invention to achieve the aforementioned objects through a novel method that is both simple and cost effective, yet results in a high recovery of pure enzyme.

It is a further object of this invention to achieve the aforementioned objects without the use of environmentally dangerous or costly chemicals or inorganic salts.

According to the invention, a composition is provided comprising a purified enzyme and an organic compound, wherein the organic compound is selected from the group consisting of carboxylic acids having at least 2 carboxyl groups, salts or esters of these carboxylic acids, amino acids, salts or esters of these amino acids and blends of two or more of these organic compounds.

Preferably the disclosed composition comprises a purified alkaline protease and lysine, lysine-HCl, aspartic acid, malonic acid, succinic acid, fumaric acid, citric acid or a sodium or potassium salt of these acids.

Also according to the invention, a method for the preparation of purified enzyme from a fermentation broth is provided, comprising forming an enzyme solution by separating the enzyme from cells and suspended solids in a fermentation broth; concentrating the resultant enzyme solution; and adding to the concentrated enzyme solution an organic compound selected from the group consisting of carboxylic acids having at least 2 carboxyl groups, salts or esters of these carboxylic acids, amino acids, salts or esters of these amino acids and blends of two or more of these organic compounds.

Preferably the disclosed method utilizes an organic compound comprising lysine, lysine-HCl, aspartic acid, malonic acid, succinic acid, fumaric acid, citric acid or a sodium or potassium salt of these acids. Still more preferably, the addition of the organic compound to the concentrated enzyme solution is under conditions including agitation and a temperature of between about 5° C. and about 50° C., and most preferably between 30° C. and 40° C.

An advantage of one embodiment of the present invention is that, for the first time, a method of enzyme purification is disclosed wherein the enzyme is precipitated by an organic compound that is a constituent of the enzyme itself.

Another advantage of the present invention is the ability to purify enzyme preparations without utilizing environmentally injurious or dangerous chemicals, thus contributing substantially to the preservation of the environment.

The invention, together with further objects and attendant advantages, will best be understood by reference to the description, drawings, examples, and tables herein. However, the invention is not limited thereto.

DETAILED DESCRIPTION

Purified enzyme should be understood to define an enzyme having substantially reduced color, probably due to the removal of pigment. The purified enzyme also has a substantially reduced content of galactosyl polymer, generally less than 1.00 milligram galactosyl polymer per gram of enzyme protein, and preferably less than 0.65 mg/g. For the purposes of illustration purified alkaline protease from *Bacillus alcalophilus* will have an absorbance of less than 1.3 at 470 nm when concentrated to an activity of 1,000,000 DU/ml, and purified alkaline protease from *Bacillus licheniformis* will have an absorbance of less than 0.5 at 470 nm when concentrated to an activity of 440 DAPU/ml.

In accordance with one embodiment of the present invention, a purified alkaline protease product is prepared as follows.

A *Bacillus alcalophilus* fermentation broth is prepared by cultivating a suitable strain in a liquid culture medium which contains components necessary for the microorganisms' growth.

After fermentation, an enzyme solution is formed by separating the enzyme from the microbial cells, various suspended solids, and residual raw fermentation materials present in the fermentation broth using conventional separation techniques. The resultant alkaline protease enzyme solution is concentrated into a concentrated enzyme solution using ultrafiltration until a suitable protease activity is obtained, which in the case of *Bacillus alcalophilus* alkaline protease is about 1,000,000 Delft units/ml ("DU/ml").

To the concentrated enzyme solution, an organic compound comprising lysine-HCl is added to a final concentration of 0.5M. The solution is adjusted to a pH of about 5.0 and the solution allowed to incubate at 30° C. for 24 hours under constant agitation by stirring. Upon the addition of lysine-HCl, the alkaline protease begins to separate out from solution as a precipitate. The enzyme precipitate is separated from the supernatant by centrifugation at 15,000 rpm for 30 minutes. The enzyme precipitate is predominantly in crystalline form and represents a highly purified enzyme product. The obtained purified alkaline protease in the precipitate represents a recovery in excess of 94% of the alkaline protease present in the unpurified concentrated alkaline protease solution prior to precipitation.

In another embodiment of the present invention, a purified alkaline protease derived from *Bacillus licheniformis* is obtained. A fermentation broth of *Bacillus licheniformis* is prepared by cultivating a suitable strain in a liquid culture medium which contains components necessary for the microorganism's growth. After fermentation, an enzyme solution is formed by separating the enzyme from the microbial cells, various suspended solids, and residual raw fermentation materials present in the fermentation broth using conventional separation techniques. The resultant alkaline protease enzyme solution is concentrated into a concentrated enzyme solution using ultrafiltration until a suitable protease activity is obtained, which in the case of *Bacillus licheniformis* is about 863 detergent alkaline protease units/ml ("DAPU/ml").

To the concentrated enzyme solution, an organic compound comprising succinic acid is added to a final concentration of 0.5M. The solution is adjusted to a pH of about 6.0 and incubated at 37° C. for 4 hours under constant agitation by stirring. Upon addition of succinic acid, the alkaline protease begins to separate out from solution in the form of a precipitate. The enzyme precipitate is separated from the supernatant by centrifugation at 20,000 rpm for 20 minutes. The enzyme precipitate represents a highly purified enzyme product and is partially crystalline. The obtained purified alkaline protease in the precipitate represents a recovery of about 86% of the total alkaline protease present in the unpurified concentrated enzyme solution prior to precipitation.

Various alternative embodiments are possible. For example, generally, the enzyme is derived from a bacterial source. In a general embodiment of the invention the enzyme is selected from the group consisting of proteases, lipases, amylases, cellulases, hemicellulases, pectinases, amidases, catalases, isomerases and oxidases. Also protein engineered variants of these enzymes are within the scope of the invention. In a preferred embodiment of the invention the enzyme is a protease, an alkaline protease or a protein engineered variant of these enzymes. In a more preferred embodiment of the invention the enzyme is the alkaline protease or the genetically engineered variant thereof derived from a *Bacillus* species. In a most preferred embodiment the enzyme is a bacterial alkaline protease, derived from *Bacillus licheniformis, Bacillus alcalophilus, Bacillus lentus, Bacillus amyloliquefaciens, Bacillus subtilis* their derivatives or a protein engineered variant of these enzymes. Good results have been obtained with bacterial alkaline proteases derived from *Bacillus licheniformis* or *Bacillus alcalophilus*. Alkaline protease derived from *Bacillus licheniformis* or *Bacillus alcalophilus* should be understood to include the natural proteases as well as their genetically engineered variants.

The enzyme should be present in the concentrated enzyme solution in a concentration sufficient to allow precipitation to occur.

Generally the organic compound present in the composition according to the invention is an organic compound selected from the group consisting of carboxylic acids having at least 2 carboxyl groups, salts or esters of these carboxylic acids, amino acids, salts or esters of these amino acids and blends of two or more of these organic compounds. The carboxylic acids are preferably chosen from among aliphatic, saturated or unsaturated carboxylic acids. The amino acids are preferably naturally occurring amino acids, of either natural or synthetic origin. The chosen organic compound should be soluble in water, i.e., it should exhibit a solubility in pure water above 5 g/l at 25° C.

The preferred organic compounds according to the invention are the naturally occurring amino acids, salts or esters of these amino acids, as they are constituents of the enzyme itself.

The naturally occurring amino acids, and salts and esters of these amino acids are generally chosen from among the acidic amino acids, basic amino acids, salts of these amino acids, esters of these amino acids and blends of two or more of these amino acids. Preferably they are chosen from among lysine, arginine, ornithine, histidine, aspartic acid, glutamic acid, methionine, phenylalanine, tyrosine, serine, their sodium and potassium salts, their chlorhydrates, lysine-HCl (chlorhydrate of lysine), L-lysine-methyl ester dihydrochloride and blends of two or more of these organic compounds. More particular preference is afforded to the naturally occurring amino acids and salts or esters of these amino acids chosen from among lysine, arginine, histidine, aspartic acid, glutamic acid, a sodium salt of these amino acids, lysine-HCl and blends of two or more of these organic compounds. Good results have been obtained with lysine, lysine-HCl and aspartic acid. The best results have been obtained with lysine and lysine-HCl.

The aliphatic, saturated or unsaturated, carboxylic acids having at least 2 carboxyl groups, and the salts and esters of these carboxylic acids, are generally chosen from among the carboxylic acids having 2 to 3 carboxyl groups and containing at least 3 carbon atoms, their sodium, calcium, potassium or magnesium salts and blends of two or more of these organic compounds. Preferably they are chosen from carboxylic acids having 2 to 3 carboxyl groups and containing 3 to 6 carbon atoms, their sodium or potassium salts and mixtures of two or more of these organic compounds. More preferably the organic compound is chosen from among malonic acid, succinic acid, citric acid, maleic acid, fumaric acid, sodium or potassium salts of these acids and blends of two or more of these organic compounds. Good results have been obtained with malonic acid, succinic acid, citric acid, a sodium salt of these acids and blends of two or more of these organic compounds. Best results have been obtained with succinic acid, citric acid or a sodium salt of these acids.

The present invention relates also to a method for the preparation of purified enzyme from a fermentation broth, comprising:

(i) forming an enzyme solution by separating the enzyme from cells and suspended solids in said fermentation broth;

(ii) concentrating said enzyme solution;

(iii) adding to said concentrated enzyme an organic compound selected from the group consisting of carboxylic acids having at least 2 carboxyl groups, salts or esters of these carboxylic acids, amino acids, salts or esters of these amino acids and blends of two or more of these organic compounds;

(iv) incubating said concentrated enzyme solution containing said organic compound; and (v) collecting a purified enzyme precipitate.

Fermentation, separation, and concentration techniques are well known in the art and conventional methods can be used to achieve the desired results.

In accordance with the preferred embodiment of the present invention, a purified alkaline protease solution is prepared. The present invention specifically contemplates fermentation mixtures of either *Bacillus licheniformis* or *Bacillus alacalophilus*.

For cultivation of strains, which produce the enzyme, usually a solid or liquid culture medium is used which contains an alkaline buffer as well as components necessary for the microorganisms growth, a carbon source, a nitrogen source and inorganic salts. Of course, the optimal nutrient mix will depend on the specific microorganism strain chosen, such information being readily available to one or ordinary skill in the art. The buffer should generally maintain the pH of the medium at a level between 7.0 and 10.0. Suitable carbon sources include mannose, fructose, mannitol, maltose, cellobiose, sucrose, dextrin, starch, molasses, glucose, hydrolysed starch or a blend of two or more of these carbon sources. Nitrogen sources which can be used include soybean flour, casein, corn steep liquor, cotton seed meal, enzymatic hydrolyzates of available proteins, dried yeast, yeast extract, fish meal, potato meal or a blend of two or more of these nitrogen sources. Examples of suitable alkaline buffers include sodium carbonate, potassium carbonate, sodium bicarbonate and sodium phosphate.

The medium containing the above components is sterilized in a conventional manner and inoculated with one of the strains of the present invention which produce enzyme. Cultivation may be conducted aerobically with shaking or under aerated agitation preferably at 30° C. to 40° C. for 30 to 120 hours to obtain a culture.

Where a high yield of a specific enzyme is desired, it may be advantageous to prepare the fermentation broth with a microorganism strain wherein the expression of that specific enzyme has been amplified. Such microorganisms are generally bacteria, and are generally prepared using techniques such as genetic engineering and bacterial transformation or selective mutation, which techniques are well known to one of ordinary skill in the art.

After fermentation the microbial cells and various suspended solids, including residual raw fermentation materials, are removed by conventional separation techniques. Filtration, centrifugation, microfiltration, rotary vacuum filtration, ultrafiltration, centrifugation followed by ultrafiltration or the like will generally suffice. In the preferred embodiment of the invention centrifugation, ultrafiltration or centrifugation followed by ultrafiltration are used. The best results are obtained with centrifugation.

It is desirable to concentrate the enzyme solution in order to optimize recovery. Use of unconcentrated solutions will require increased incubation time in order to collect the purified enzyme precipitate.

The enzyme solution is concentrated into a concentrated enzyme solution using conventional concentration techniques until the desired enzyme activity is obtained. Concentration of the enzyme solution may be achieved by any of a variety of conventional techniques including filtration, centrifugation, microfiltration, rotary vacuum filtration, ultrafiltration, centrifugation followed by ultrafiltration, evaporation, extraction or chromatography. In the preferred embodiment of the invention centrifugation and/or ultrafiltration is used. In the most preferred embodiment of the invention ultrafiltration is used. The enzyme should be present in the concentrated enzyme solution in a concentration sufficient to allow precipitation to occur. For the alkaline protease derived from *Bacillus alcalophilus* the enzyme solution is concentrated into a concentrated enzyme solution until the enzyme activity is usually at least about 250,000 DU/ml and preferably at least about 750,000 DU/ml. The best results have been obtained with an enzyme activity of about 1,000,000 DU/ml. For the alkaline protease derived from *Bacillus licheniformis* the enzyme solution is concentrated into a concentrated enzyme solution until the enzyme activity is about 250 DAPU/ml and preferably at least about 300 DAPU/ml. The best results have been obtained with an enzyme activity of at least about 400 DAPU/ml.

The concentrated enzyme solution is combined with the organic compound according to the invention.

The selection of at least an effective amount and an optimum amount of organic compound effective to cause precipitation of the enzyme and the conditions of the precipitation for maximum recovery including incubation time, pH, temperature, and concentration of enzyme will be readily apparent to one of ordinary skill in the art, in light of the present disclosure, after simple routine testing.

Generally the concentration of the organic compound is at least 0.06M, usually between about 0.07M and 1M. For the alkaline proteases the organic compound is added usually to a final concentration of between about 0.08M and 0.9M, and preferably to a final concentration of between about 0.09M and 0.8M. For the alkaline proteases derived from *Bacillus licheniformis* the organic compound is added preferably to a final concentration of between about 0.09M and 0.75M. For the alkaline proteases derived from *Bacillus alcalophilus* the organic compound is added preferably to a final concentration of between about 0.25M and 0.8M.

The optimal concentration of the organic compound added to purify a desired enzyme will depend on the nature of the specific enzyme, its structure, stability and chemistry. For example *Bacillus alcalophilus* alkaline protease generally requires lysine in a concentration of 0.5M to precipitate out of solution, whereas *Bacillus licheniformis* may be substantially precipitated out of solution upon, the addition of as little as 0.1M. Also, the optimal concentration of organic compound and the reaction conditions for purification of a desired enzyme will depend on the specific organic compound used, its structure and chemistry, and particularly its hydrophobicity.

The solution is adjusted to a pH which will, of necessity, depend on the enzyme to be purified and the organic compound used, as explained above. For alkaline proteases, the solution is adjusted usually to a pH of between about 3.5 and 10.5. Preferably the solution is adjusted to a pH of between about 4 and 10. For alkaline protease derived from *Bacillus licheniformis* good results have been obtained with a pH of between about 5.5 and 9.5. For the alkaline protease derived from *Bacillus alcalophilus* good results have been obtained with a pH of between about 4 and 9.5.

Generally the temperature during precipitation is between about 5° C. and about 50° C., usually the method is carried out at a temperature between about 20° C. and about 45° C., and preferably between about 28° C. and about 40° C. The optimal temperature for inducing precipitation will vary according to the solution conditions and the enzyme or organic compound used. For example, alkaline protease derived from *Bacillus alcalophilus* will be substantially precipitated after incubation for six hours at a temperature between 20° C. and 40° C.

In an alternative embodiment of the present invention, hydrolytic enzymes can be added to the concentrated enzyme solution. Thus, step (iii) can further comprise adding to the concentrated enzyme solution at least one hydrolytic enzyme. The addition of these hydrolytic enzymes can take place prior to or simultaneously with the addition of the organic compound, and enzymatic hydrolysis and the addition of the organic compound may be carried out sequentially or simultaneously. The purpose of adding hydrolytic enzymes is to hydrolyse polymeric impurities that are undesirable, such as cell wall anionic polymers, peptidoglycans, galactose polymer and other poly- and oligosaccharide contaminants that become solubilized during the fermentation of microorganisms. Suitable hydrolytic enzymes are enzymes which hydrolyse polysaccharides including oligosaccharides, amylases, alpha-amylases, pullulanases, transferases, polysaccharide hydrolases, glycohydrolases, galactosyl hydrolases, pectinases, gluconases, glucoamylases or blends of two or more these hydrolytic enzymes. Examples of preferred hydrolytic enzymes are CLAREX pectinase and DIAZYME L-200 glucoamylase, enzymes available from Solvay Enzymes, Inc., Elkhart, Ind.

According to this embodiment, the enzyme solution may be maintained at a constant pH and temperature throughout the incubation period subsequent to the addition of the organic compound. During the incubating period, the enzyme is separated from hydrolyzed polymeric impurities and dissociated from pigments. Under this embodiment, it is desirable to allow the concentrated enzyme solution including hydrolytic enzymes to incubate for between 48 and 72 hours to ensure complete hydrolysis of galactosyl polymer.

The time of incubation necessary to obtain a purified enzyme precipitate according to the present invention will not only depend on the nature of the specific enzyme and its concentration but also on the specific organic compound added and its concentration. Generally a 1 to 48 hour incubation period is required for precipitation, usually a 2 to 32 hour period, and preferably a 3 to 25 hour period. For example, alkaline protease derived from *Bacillus alcalophilus* will generally be substantially precipitated after incubation for 15–20 hours, where the precipitant is lysine in a concentration of 0.5M, and the incubation conditions include a pH of 5.0 and a temperature of 30° C. Alkaline protease from *Bacillus licheniformis* will precipitate out in a similar time period where the precipitant is lysine in a concentration of 0.5M, and the incubation conditions include a pH of 6.0 and a temperature of 25° C. Where the precipitant is succinic acid in a concentration of 0.5M, alkaline protease from *Bacillus licheniformis* will precipitate out in about four hours under incubation conditions including a pH of 6.0 and a temperature of 37° C.

The overall recovery of purified enzyme precipitate and the efficiency with which the process is conducted will be improved by agitating the solution comprising the enzyme and the added organic compound, both during addition of the organic compound and during the subsequent incubation period. Suitable agitation methods include mechanical stirring or shaking, vigorous aeration or any similar art recognized technique.

After the incubation period, the purified enzyme is separated from the dissociated pigment and other impurities and collected by conventional separating techniques, such as filtration, centrifugation, microfiltration, rotary vacuum filtration, ultrafiltration, press filtration, cross membrane microfiltration, cross flow membrane microfiltration, centrifugation followed by ultrafiltration or the like. In the preferred embodiment of the invention filtration is used. Cross membrane microfiltration has been utilized for this purpose with excellent results. Further purification of the purified enzyme precipitate can be obtained by washing the precipitate with water, preferably with water containing the organic compound.

As indicated above, where the organic compound added to precipitate the enzyme is an amino acid, the resultant purified enzyme product is predominantly crystalline. Similarly, the enzyme product obtained where a dicarboxylic acid is added contains a degree of crystallinity. As such, standard techniques of increasing crystal yield may be utilized. For example, the use of seed crystals results in more favorable kinetics for the crystallization process. Utilization of a reaction vessel having certain surface properties is also advantageous, these properties being apparent to one of ordinary skill in the art. Crystal growth may also be advantageously promoted by agitation of the crystallization vessel. Promotion of a greater proportion of crystallinity in the precipitate is advantageous because crystalline products are easier to utilize and handle with respect to incorporation into commercial products.

Purified enzyme solids or compositions according to one of the embodiments of the present invention are useful for all applications to which enzymes are utilized in either solid or liquid form. These preparations can be made into a final product that is either liquid solution, solid, granular, powder or a slurry. For example, they can be used in laundry detergents and spot removers, as contact lens enzymatic cleansing systems, as a depilatory in tanning, in the food industry, and in blood serum testing procedures for the detection of incomplete antibodies.

Alkaline proteases prepared according to the present invention are particularly useful in detergents and cleansers due to lessened pigment content and thus have a reduced level of haze formation, odor and color contamination. Moreover, the removal of galactosyl polymers and their allergenic properties from enzyme preparations prepared according to the embodiments of this invention is especially useful in preparing enzymatic contact lens products and other commercial applications, and also in the food, feed and detergent industries.

In the detergent applications, alkaline proteases prepared according to the invention are usually used in a liquid composition containing propylene glycol. The alkaline protease is solubilized preferably in propylene glycol by circulating in a 25% volume/volume propylene glycol solution containing 10% calcium chloride.

In the contact lens enzymatic cleaning systems applications, enzymes prepared according to the present invention are usually dried. Preferably they are dried by lyophilization. The product may also be prepared in granulated form such as that described in U.S. Pat. No. 4,689,297 to Goode et al., entitled "Dust Free Particulate Enzyme Formulation," issued Aug. 25, 1987, which is herein incorporated by reference. Further, the product may be in the form of a slurry which includes suspended insoluble enzyme in water.

The following examples, related tables, and drawings are intended to further illustrate the invention. It will be understood, however, that the invention is not limited to these specific examples or the embodiments expressed therein.

EXAMPLE 1

The effect of varying concentrations of lysine on enzyme precipitation was studied. A fermentation broth was produced in a submerged culture of *Bacillus alcalophilus* in a suitable medium. After fermentation, an enzyme solution was formed by separating the enzyme from the microbial cells, suspended solids, and other residual fermentation raw material, using conventional means such as centrifugation and vacuum drum filtration. A concentrated enzyme solution was then formed of the resultant alkaline protease solution by ultrafiltration to an activity of 1,000,000 DU/ml. Lysine was added at varying final concentrations to the concentrated enzyme solution. The pH of the concentrated enzyme solution was adjusted to 5.0 using dilute acetic acid at 10% volume/volume. The treated samples were then incubated at 30° C. under constant agitation by stirring with a magnetic stirrer.

After incubation for 24 hours, the predominantly crystalline enzyme precipitate was separated from the supernatant by centrifugation at 15,000 rpm for 30 minutes. The precipitate was then solubilized in propylene glycol at a pH of 5.0 and stirred for 12 hours at room temperature. The percentage recovery in the purified *Bacillus alcalophilus* alkaline protease precipitate was determined through an assay based on the hydrolysis of a casein substrate.

Enzyme activity was determined based on the Delft Unit (DU). A casein solution was hydrolyzed by the unprecipitated alkaline protease in the supernatant at a temperature of 40° C. and in a borate buffer at a pH of 8.5. Unhydrolyzed casein was precipitated with trichloroacetic acid and removed by centrifugation. The absorbance of the trichloroacetate soluble casein-hydrolysate was measured in a spectrophotometer at 275 nm. If 1 ml of a 2% solution of an enzyme preparation gives a difference in absorbance of 0.4 under the test conditions, then the protease preparation has an activity of 1000 DU. The total alkaline protease activity value (DU/ml) of the supernatant solution was compared to the activity of a non-precipitated control to determine the percentage recovery in the precipitate.

The effect of lysine concentration on the amount of protease precipitate is shown in Table 1.

TABLE 1

| Recovery of Purified Alkaline Protease Precipitate Using Lysine ||
|---|---|
| Lysine Concentration Molarity | Percent Recovery In Purified Precipitate |
| 0.1 | 1.5 |
| 0.2 | 1.7 |

TABLE 1-continued

Recovery of Purified Alkaline Protease Precipitate Using Lysine

| Lysine Concentration Molarity | Percent Recovery In Purified Precipitate |
|---|---|
| 0.3 | 68.0 |
| 0.4 | 85.0 |
| 0.5 | 88.0 |

EXAMPLE 2

The addition of lysine to the concentrated enzyme solution of Example 1 caused an increase in the pH, necessitating a pH adjustment to maintain the pH at 5.0. Lysine-HCl was utilized to purify the enzyme, and the recovery compared to a sample precipitated using only lysine. A concentrated enzyme solution of alkaline protease from Bacillus alcalophilus with an activity of 1,000,000 DU/ml was prepared. Lysine and lysine-HCl were added to separate aliquots to a final concentration of 0.5M. The pH was adjusted to 5.0 and the solution incubated at 30° C. for 24 hours under constant agitation by stirring. The predominantly crystalline alkaline protease precipitates were separated by centrifugation, and the activity measured to determine the percentage recovery. Results are shown in Table 2.

TABLE 2

Comparison Of Lysine And Lysine-HCl Precipitation Effect

| Organic compound | Percent Recovery In Precipitate |
|---|---|
| Lysine | >94 |
| Lysine-HCl | >94 |

The difference in the amount of crystallized enzyme obtained varied insubstantially between purification with lysine and purification with the lysine-HCl. Thus, it may be advantageous to utilize Lysine-HCl to avoid the necessity of readjusting the pH.

EXAMPLE 3

The effect of pH on enzyme precipitation was studied. A concentrated enzyme solution of alkaline protease from Bacillus alcalophilus with an activity of 1,000,000 DU/ml was prepared. Lysine-HCl was added to a final concentration of 0.4M. The pH of the separate aliquots of solution was adjusted to 4.5, 5.0, 5.5, 6.0, 7.0, 8.0, 9.0 and 10.0 using 20% weight/volume sodium hydroxide. After stabilizing the pH, the treated samples were incubated at 30° C. for 24 hours under constant agitation by stirring. The predominantly crystalline alkaline protease precipitates were separated by centrifugation from the supernatants, and the activity was measured to determine the percent recovery. Results are shown in Table 3.

TABLE 3

Effect Of pH On Purification Of Alkaline Protease

| pH During Incubation | Percent Recovery In Precipitate |
|---|---|
| 4.5 | 85 |
| 5.0 | 88 |
| 5.5 | 93 |
| 6.0 | 83 |
| 7.0 | 73 |
| 8.0 | 63 |
| 9.0 | 69 |
| 10.0 | 5 |

As shown in Table 3, maximum precipitation of Bacillus alcalophilus alkaline protease occurred in the acidic pH ranges.

EXAMPLE 4

The effect of L-lysine-methyl ester dihydrochloride on enzyme precipitation was studied. A concentrated enzyme solution of alkaline protease from Bacillus alcalophilus with an activity of 1,000,000 DU/ml, obtained according to the conditions of the example 1, was prepared. L-lysine and L-lysine-methyl ester dihydrochloride were added separately to a final concentration of 0.5M.

The pH of the solutions was adjusted to pH of 5.5 and the solutions were incubated at 30° C. for 24 hours under constant agitation by stirring. The protease precipitates were separated by centrifugation at 15,000 rpm for 20 minutes from the supernatants and the enzyme activity measured to determine the percent recovery. The results are summarized in Table 4.

TABLE 4

Effect of Lysine Derivative On Enzyme Precipitation

| Organic Compound | Percent Recovery In Precipitate |
|---|---|
| L-Lysine | 95 |
| L-Lysine-methyl ester dihydrochloride | 76 |

EXAMPLE 5

The effect of different concentrations of lysine on the precipitation of enzyme was studied. A concentrated enzyme solution of alkaline protease from Bacillus licheniformis with an activity of 500 DAPU/ml was prepared. Lysine was added to the concentrated enzyme solutions to final concentrations of 0.01M, 0.05M, 0.1M, 0.2M and 0.5M. The pH of each solution was adjusted to 6.0 and the solutions incubated at 25° C. for 24 hours under constant agitation by stirring. The predominantly crystalline alkaline protease precipitates were separated from the supernatants by centrifugation, and the activity measured to determine the percent recovery. Results are shown in Table 5.

The percent recovery in the Bacillus licheniformis alkaline protease precipitate was determined through an assay based on hydrolysis of a casein substrate at 40° C., at pH 8.5 (borate buffer). Casein was hydrolyzed by the unprecipitated alkaline protease in the supernatant. Unhydrolyzed casein was precipitated with trichloroacetic acid and removed by centrifugation. The absorbance of the trichloroacetate soluble casein-hydrolysate was measured in a spectrophotometer at 275 nm. One detergent alkaline protease unit (DAPU) is that activity which will liberate the equivalent of four micromoles of tyrosine per minute under the conditions of the assay. The total alkaline protease activity value (DAPU/ml) of the supernatant solution was compared to the activity of a non-precipitated control to determine the percentage recovery.

TABLE 5

Effect Of Lysine Concentration on Enzyme Precipitation

| Lysine Concentration Molarity | Percent Recovery In Precipitate |
|---|---|
| 0.01 | 3 |
| 0.05 | 29 |
| 0.10 | 45 |

TABLE 5-continued

Effect Of Lysine Concentration on Enzyme Precipitation

| Lysine Concentration Molarity | Percent Recovery In Precipitate |
|---|---|
| 0.2 | 67 |
| 0.5 | 89 |

EXAMPLE 6

The effect of organic acids containing dicarboxylic acids on enzyme precipitation was studied. A concentrated enzyme solution of *Bacillus licheniformis* alkaline protease with an activity of 863 DAPU/ml was prepared. To separate aliquots of the concentrated enzyme solution, malonic acid (HOOC—CH$_2$—COOH), succinic acid (HOOC—(CH$_2$)$_2$—COOH) and glutaric acid (HOOC—(CH$_2$)$_3$—COOH) were added to final concentrations of 0.5M. The solutions were adjusted to a pH of 6.0 and incubated at 37° C. for 4 hours under constant agitation by stirring. The enzyme precipitates were separated from the supernatants, and the activity measured to determine percent recovery. Results are shown in Table 6.

TABLE 6

Effect Of Certain Dicarboxylic Acids On Enzyme Precipitation

| Dicarboxylic Acid | Structural Formula HOOC—(CH$_2$)$_n$—COOH | Percent Recovery In Precipitate |
|---|---|---|
| Malonic | HOOC—CH$_2$—COOH | 73 |
| Succinic | HOOC—(CH$_2$)$_2$—COOH | 70 |
| Glutaric | HOOC—(CH$_2$)$_3$—COOH | 55 |

EXAMPLE 7

The effect of adding organic acids containing multiple carboxyl groups on the precipitation of enzyme was studied. A concentrated solution of alkaline protease from *Bacillus licheniformis* with an activity of 440 DAPU/ml was prepared. To separate aliquots of the concentrated enzyme solution, sodium salts of a monocarboxylic acid (acetic acid), two dicarboxylic acids (malonic acid and succinic acid) and a tricarboxylic acid (citric acid) were added to a final concentration of 0.5M. The solutions were adjusted to a pH of 6.0 and incubated at 37° C. for 4 hours under constant agitation by stirring. The enzyme precipitates were separated from the supernatant, and the protein content, protease activity, and the percentage recovery determined. Results are shown in Table 7.

A protein-dye binding method was used to quantitate the total proteins. (Bradford, Anal. Biochim; 72,248, 1976). An aliquot of protein solution (0.1 ml) was pipetted into a test tube and 5 ml of a protein-dye reagent added thereto and mixed on a vortex mixer. The absorbance at 595 nm was measured after 5 minutes against a reagent blank prepared from 0.1 ml of water and 5 ml of protein-dye reagent. The amount of the protein was then determined from a standard curve prepared from bovine gamma globulin.

TABLE 7

Effect of An Increasing Degree of Carboxyl Group Substitution On Enzyme Precipitation

| Carboxylic Acid (0.5M) | Structural Formula | Protein mg/ml In The Supernatant | Protein Percent Recovery In Precipitate | Alkaline Protease DAPU/ml In The Supernatant | Alkaline Protease Percent Recovery In Precipitate |
|---|---|---|---|---|---|
| Control | — | 63.0 | 0 | 440 | 0 |
| Acetic acid | CH$_3$—COOH | 39.7 | 37 | 277 | 37 |
| Malonic acid | HOOC—CH$_2$—COOH | 16.9 | 73 | 118 | 73 |
| Succinic acid | HOOC—CH$_2$—CH$_2$—COOH | 18.9 | 70 | 132 | 70 |
| Citric acid | CH$_2$—COOH<br>\|<br>CH—COOH<br>\|<br>CH$_2$—COOH | 10.0 | 84 | 63 | 86 |

As shown in Table 7, the precipitation of enzyme increased with an increasing degree of substitution of the acid with carboxyl groups. Better results have been obtained with dicarboxylic acids and tricarboxylic acids than with monocarboxylic acids.

EXAMPLE 8

The effect of adding carboxylic acids containing a double bond on the precipitation of enzyme was studied. A concentrated enzyme solution of alkaline protease from *Bacillus licheniformis* with an activity of 453 DAPU/ml was prepared. Sodium salts of acrylic acid, maleic acid, and fumaric acid, were added to separate aliquots of the concentrated enzyme solution to final concentrations of 0.5M. The solutions were adjusted to a pH of 6.0 and incubated at 37° C. for 4 hours under constant agitation by stirring. The enzyme precipitates were separated from the supernatant, and the total protein, protease activity, and the percent recovery determined. Results are shown in Table 8. Maleic acid and fumaric acid, both unsaturated dicarboxylic acids, precipitated the enzyme. However, acrylic acid, an unsaturated monocarboxylic acid, had no effect on the solubility of alkaline protease and no precipitate was obtained.

TABLE 8

Effect of Unsaturated Carboxylic Acids on Enzyme Precipitation

| Unsaturated Organic Acid (0.5M) | Structural Formula | Protein mg/ml In The Supernatant | Protein Percent Recovery In Precipitate | Protease Activity DAPU/ml In The Supernatant | Protease Activity Percent Recovery In Precipitate |
|---|---|---|---|---|---|
| Control | — | 58 | 0 | 453 | 0 |
| Acrylic acid | H$_2$C=CH—COOH | 57 | 2 | 455 | 0 |

TABLE 8-continued

Effect of Unsaturated Carboxylic Acids on Enzyme Precipitation

| Unsaturated Organic Acid (0.5M) | Structural Formula | Protein mg/ml In The Supernatant | Percent Recovery In Precipitate | Protease Activity DAPU/ml In The Supernatant | Percent Recovery In Precipitate |
|---|---|---|---|---|---|
| Maleic acid | CH—COOH \|\| CH—COOH (Cis) | 30.0 | 52 | 222 | 49 |
| Fumaric acid | HOOC—CH \|\| HC—COOH (Trans) | 18.6 | 68 | 163 | 64 |

EXAMPLE 9

The effect of pH on the ability of succinic acid to precipitate enzyme was studied. A concentrated enzyme solution of alkaline protease from *Bacillus licheniformis* with an activity of 750 DAPU/ml was prepared. Succinic acid was added to the concentrated enzyme solution to a final concentration of 0.25M. Separate 100 ml aliquots were adjusted to pH levels of 4.0, 5.0, 6.0, 7.0, 8.0 and 9.0 using 20% sodium hydroxide and the solutions incubated at a temperature of 30° C. for 20 hours under constant agitation by stirring. The enzyme precipitates were separated from the supernatant, and the activity measured to determine the percent recovery. Results are shown in Table 9.

TABLE 9

Effect Of pH On Enzyme Precipitation

| pH Of The Precipitation | Percent Recovery In Precipitate |
|---|---|
| 4.0 | 0.8 |
| 5.0 | 5.7 |
| 6.0 | 71 |
| 7.0 | 81 |
| 8.0 | 92 |
| 9.0 | 94 |

As shown in Table 9, maximum precipitation of the alkaline protease derived from *Bacillus licheniformis* occurred in the basic pH ranges.

EXAMPLE 10

The effect of time on the precipitation of enzyme with lysine was studied. A concentrated enzyme solution of alkaline protease from *Bacillus alcalophilus* with an activity of 1,000,000 DU/ml was prepared. Lysine was added to a final concentration of 0.5M. The solution was adjusted to a pH of 5.0 and incubated at 30° C. The enzyme precipitates were separated from the supernatant, and the activity measured to determine the percent recovery. Results are shown in Table 10.

TABLE 10

| Incubation Time In Hours | Percent Recovery In Precipitate |
|---|---|
| 10 | 73 |
| 15 | 90 |
| 24 | 89.5 |
| 36 | 91 |
| 48 | 94 |

As shown in Table 10, a substantial portion of the enzyme appeared in the precipitate in from 10-20 hours.

EXAMPLE 11

The effect of temperature on the precipitation of enzyme with lysine was studied. A concentrated enzyme solution of alkaline protease from *Bacillus alcalophilus* with an activity of 1,000,000 DU/ml was prepared. Lysine was added to a final concentration of 0.5M. Separate aliquots of the solution were adjusted to a pH of 5.0, and incubated at varying temperatures for 6 hours. The enzyme precipitates were separated from the supernatant, and the activity measured to determine the percent recovery. Results are shown in Table 11.

TABLE 11

| Temperature Of Incubation °C. | Percent Recovery In Precipitate |
|---|---|
| 5 | 1 |
| 20 | 65 |
| 30 | 73 |
| 35 | 94 |
| 40 | 91 |

As shown in Table 11 substantial precipitation occurred between 20° C. and 40° C. under these conditions.

EXAMPLE 12

Alkaline protease is produced from a fermentation broth of a submerged culture of *Bacillus licheniformis* in a suitable medium. After the fermentation the microbial cells and suspended solids are separated from the alkaline protease by centrifugation. The resultant alkaline protease solution is then concentrated using ultrafiltration. An aqueous solution of alkaline protease concentrate having an enzymatic activity of 880 DAPU/ml is obtained.

Different amounts of amino acids are added to 30 ml of this concentrated enzyme solution at a pH of 6.0. The pH of the solution is maintained at a pH of 6.0 using sodium hydroxide. The volume of the solution is adjusted to 50 ml with water and incubated at 37° C. for 4 hours under constant agitation. The enzyme precipitate is separated by centrifugation at 20,000 rpm for 20 minutes at 5° C.

The clear supernatant is analyzed for protein and enzyme activity. The results are summarized in Table 12.

TABLE 12

Effect of amino acids on enzyme precipitation

| Amino acid | concentration (molarity) | Protein mg/ml In The Supernatant | Protein Percent Recovery In Precipitate | Protease Activity DAPU/ml In The Supernatant | Protease Activity Percent Recovery In Precipitate |
| --- | --- | --- | --- | --- | --- |
| Control | 0 | 74.0 | 0 | 500 | 0 |
| Aspartic acid | 0.50 | 36.7 | 50 | 253 | 49 |
| Aspartic acid | 0.75 | 30.0 | 59 | 208 | 58 |
| Lysine | 0.50 | 30.0 | 59 | 208 | 58 |

EXAMPLE 13

The effect of adding monocarboxylic acids on the precipitation of enzyme was studied. A concentrated solution of alkaline protease from *Bacillus licheniformis* with an activity of 440 DAPU/ml was prepared. Sodium salts of two monocarboxylic acids, acetic acid and formic acid, were added to a final concentration of 0.5M. The pH of the solution was adjusted to 6.0 and the solution was incubated at 37° C. for 4 hours under conditions of constant agitation by stirring. The enzyme precipitate was separated by centrifugation from the supernatant and the protein content, protease activity and percentage recovery were determined. Results are shown in Table 13.

TABLE 13

| Monocarboxylic Acid | Protein mg/ml In The Supernatant | Protein Percent Recovery In Precipitate | Protease activity DAPU/ml In The Supernatant | Protease activity Percent Recovery In Precipitate |
| --- | --- | --- | --- | --- |
| control | 70 | 0 | 488 | 0 |
| acetic acid | 45.0 | 36 | 306 | 37 |
| formic acid | 42.0 | 40 | 291 | 40 |

Comparison of the results of comparative example 13 with those of example 7, performed under identical conditions, shows that far better results are obtained using an organic compound according to the invention as a precipitation agent.

Of course, it should be understood that a wide range of changes and modifications can be made to the preferred embodiments described above. It is therefore intended that the foregoing detailed description be understood that it is the following claims, including all equivalents, which are intended to define the scope of this invention.

We claim:

1. A method for the recovery of purified hydrolase from a fermentation broth, comprising the following steps:
   (i) forming a hydrolase solution by separating the hydrolase from cells and suspended solids in said fermentation broth,
   (ii) concentrating said hydrolase solution,
   (iii) adding to said concentrated hydrolase solution an organic compound comprising a carboxylic acid having at least 2 carboxyl groups, a salt or ester of these carboxylic acids, an amino acid, a salt or ester of these amino acids or a blend of two or more of these organic compounds in order to facilitate precipitation of said hydrolase,
   (iv) incubating said concentrated hydrolase solution containing said organic compound, wherein a purified hydrolase precipitate is formed, and
   (v) collecting a purified hydrolase precipitate.

2. The method according to claim 1, wherein step (iii) is carried out at a pH from about 3.5 to 10.5.

3. The method according to claim 1, wherein steps (iii) and (iv) further comprise agitation.

4. The method according to claim 1, wherein during step (iii) the organic compound is added to a final concentration of at least 0.06M.

5. The method according to claim 1, wherein step (iii) is carried out at a temperature between about 5° C. and about 50° C.

6. The method according to claim 1, wherein it comprises after the step (v) the step (vi) consisting in washing the purified enzyme precipitate with water containing the organic compound.

7. The method according to claim 1, wherein the organic compound is selected from naturally occurring amino acids, salts or esters of these amino acids chosen from among acidic amino acids, basic amino acids, salts of them, esters of them and blends of two or more of these organic compounds.

8. The method according to claim 7, wherein the organic compound is selected from the group consisting of lysine, arginine, histidine, aspartic acid, glutamic acid, their sodium salts, lysine-HCl and blends of two or more of these organic compounds.

9. The method according to claim 8, wherein the organic compound is selected from the group consisting of aspartic acid, lysine and lysine-HCl.

10. The method according to claim 1, wherein the organic compound is selected from carboxylic acids and salts of these carboxylic acids chosen from among carboxylic acids having 2 to 3 carboxyl groups and containing at least 3 carbon atoms, their sodium, calcium, potassium or magnesium salts and blends of two or more of these organic compounds.

11. The method according to claim 10, wherein the organic compound is selected from the group consisting of malonic acid, succinic acid, citric acid, maleic acid, fumaric acid, their sodium or potassium salts and blends of two or more of these organic compounds.

12. The method according to claim 11, wherein the organic compound is selected from the group consisting of succinic acid, citric acid and a sodium salt of these acids.

13. The method according to claim 1, wherein the hydrolase is the alkaline protease derived from *Bacillus alcalophilus* or mutants thereof and wherein during step (ii) the hydrolase solution is concentrated into a concentrated hydrolase solution until the hydrolase activity is at least about 250,000 DU/ml.

14. The method according to claim 1, wherein the hydrolase is the alkaline protease derived from *Bacillus licheniformis* or mutants thereof and wherein during step (ii) the hydrolase solution is concentrated into a concentrated hydrolase solution until the hydrolase activity is at least about 250 DAPU/ml.

15. The method according to claim 1, wherein step (iii) further comprises adding to said concentrated hydrolase solution at least one hydrolytic enzyme.

16. The method according to claim 1, wherein said purified hydrolase is derived from a *Bacillus alcalophilus* or *Bacillus licheniformis* or mutants thereof fermentation broth.

17. The method according to claim 16, wherein said hydrolase is derived from a *Bacillus alcalophilus* or mutants thereof fermentation broth and said purified hydrolase collected during step (v) has an absorbance of less than 1.3 at 470 nm when concentrated to an activity of about 1,000,000 DU/ml.

18. The method according to claim 16, wherein said purified hydrolase is derived from a *Bacillus licheniformis* or mutants thereof fermentation broth, and said purified hydrolase collected during step (v) has an absorbance of less than 0.5 at 470 nm when concentrated to an activity of 440 DAPU/ml.

19. A method for the recovery of purified alkaline protease derived from *Bacillus alcalophilus* or *Bacillus licheniformis* or mutants thereof from a fermentation broth, comprising the following steps:

(i) forming an alkaline protease solution by separating the alkaline protease from cells and suspended solids in said fermentation broth, (ii) concentrating said alkaline protease solution, (iii) adding to said concentrated alkaline protease solution an organic compound comprising a carboxylic acid having at least 2 carboxyl groups, a salt or ester of these carboxylic acids, an amino acid, a salt or ester of these amino acids or a blend of two or more of these organic compounds, in order to facilitate precipitation of said alkaline protease, (iv) incubating said concentrated alkaline protease solution containing said organic compound, wherein a purified alkaline protease precipitate is formed, and (v) collecting a purified alkaline protease precipitate.

20. The method according to claim 1 wherein the hydrolase is chosen from among the group consisting of proteases, lipases, amylases, cellulases, hemicellulases, pectinases and amidases.

* * * * *